US012357385B2

(12) United States Patent
Liu et al.

(10) Patent No.: US 12,357,385 B2
(45) Date of Patent: Jul. 15, 2025

(54) SURGICAL GUIDE

(71) Applicant: SHENZHEN FUTURTEC MEDICAL CO., LTD., Shenzhen (CN)

(72) Inventors: Yanzhi Liu, Shenzhen (CN); Donghui Sun, Shenzhen (CN); Wei Huang, Shenzhen (CN); Shengxiao Zhu, Shenzhen (CN)

(73) Assignee: SHENZHEN FUTURTEC MEDICAL CO., LTD., Shenzhen (CN)

( * ) Notice: Subject to any disclaimer, the term of this patent is extended or adjusted under 35 U.S.C. 154(b) by 392 days.

(21) Appl. No.: 17/624,320

(22) PCT Filed: May 11, 2020

(86) PCT No.: PCT/CN2020/089607
§ 371 (c)(1),
(2) Date: Dec. 31, 2021

(87) PCT Pub. No.: WO2021/217713
PCT Pub. Date: Nov. 4, 2021

(65) Prior Publication Data
US 2022/0354580 A1    Nov. 10, 2022

(30) Foreign Application Priority Data

Apr. 26, 2020  (CN) .......................... 202010339289.5

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/20* (2016.02); *A61B 90/94* (2016.02);
(Continued)

(58) Field of Classification Search
CPC .................... A61B 90/11; A61B 90/94; A61B 2090/3916; A61B 2090/3983; A61B 2017/3407; A61B 2017/568
See application file for complete search history.

(56) References Cited

U.S. PATENT DOCUMENTS

| 10,136,950 | B2* | 11/2018 | Schoenefeld | ...... A61B 17/1703 |
| 2014/0350614 | A1* | 11/2014 | Frey | ........................ G06F 30/00 |
| | | | | 606/86 R |
| 2015/0150641 | A1* | 6/2015 | Daon | ...................... A61B 34/20 |
| | | | | 600/424 |

(Continued)

FOREIGN PATENT DOCUMENTS

| CN | 105411678 A | 3/2016 |
| CN | 107595389 A | 1/2018 |

(Continued)

*Primary Examiner* — Sameh R Boles
(74) *Attorney, Agent, or Firm* — Cheng-Ju Chiang (57) ABSTRACT

A surgical navigation system comprising a positioning marker on a surgical instrument, a tracer on a bone, a binocular camera, and a computer. The tracer has a navigation tracer surface. The positioning marker comprises a navigation surface. The binocular camera is connected to the computer, and transmits acquired information of the tracer and the positioning marker to the computer. The computer and a computer readable storage medium each separately store a computer program for performing a surgical navigation method: generating three-dimensional models of a bone and the surgical instrument, and obtaining tracer registration information and calibration information of the positioning marker; receiving real-time information of the tracer and the positioning marker acquired by the binocular camera; and calculating spatial position of the bone and the surgical instrument, and fusing, in real-time, the information with the three-dimensional models to obtain dynamic images of a real-time positional relationship therebetween.

5 Claims, 5 Drawing Sheets

(51) Int. Cl.
  *A61B 90/94* (2016.01)
  *A61B 17/34* (2006.01)
  *A61B 17/56* (2006.01)
  *A61B 90/00* (2016.01)
  *A61B 90/11* (2016.01)

(52) U.S. Cl.
  CPC ............ *A61B 2017/3407* (2013.01); *A61B 2017/568* (2013.01); *A61B 2034/105* (2016.02); *A61B 2034/107* (2016.02); *A61B 2034/2055* (2016.02); *A61B 2034/2068* (2016.02); *A61B 90/11* (2016.02); *A61B 2090/3916* (2016.02); *A61B 2090/3983* (2016.02)

(56) References Cited

U.S. PATENT DOCUMENTS

| | | | | |
|---|---|---|---|---|
| 2015/0223906 | A1* | 8/2015 | O'Neill | A61B 6/0492 |
| | | | | 600/407 |
| 2016/0191887 | A1 | 6/2016 | Casas | |
| 2017/0303859 | A1* | 10/2017 | Robertson | A61B 5/6819 |
| 2020/0360105 | A1* | 11/2020 | Frey | A61B 17/7067 |

FOREIGN PATENT DOCUMENTS

| | | |
|---|---|---|
| CN | 108478281 A | 9/2018 |
| CN | 108742876 A | 11/2018 |
| CN | 109152615 A | 1/2019 |
| CN | 109925055 A | 6/2019 |
| CN | 110248618 A | 9/2019 |
| CN | 110946654 A | 4/2020 |

\* cited by examiner

SURGICAL GUIDE

CROSS REFERENCE TO RELATED APPLICATIONS

The present invention is a 35 U.S.C. § 371 National Phase conversion of International (PCT) Patent Application No. PCT/CN2020/089607, filed on May 11, 2020, which claims benefit of Chinese Application No. 202010339289.5, filed on Apr. 26, 2020, the disclosure of which is incorporated by reference herein. The PCT International Patent Application was filed and published in Chinese.

FIELD OF THE INVENTION

The present invention relates to the field of medical device, specifically relates to a surgical navigation system that can be used in orthopedic surgery, and particularly to a navigation system for orthopedic surgery based on a 3D-printed tracer and optical positioning technology, a method for performing the navigation system, a computer, and a storage media.

BACKGROUND OF THE INVENTION

With the development of modern medicine and computer technology, medical imaging technology and computer image processing technology are gradually being applied to the medical field. Computer-assisted surgery technology has become a major development direction in surgery. This technology extends the limited vision of surgeons, breaks through the boundaries of traditional surgery, and redefines the surgery and surgical instruments. It is of great significance for improving the accuracy of surgical positioning, reducing surgical trauma, shortening operation duration, and improving surgical success rate.

The surgical navigation system, that is, a surgical system that uses computer-assisted technology, has now been used in spine, pelvic or thoracic surgery, joint surgery, trauma surgery, bone tumors or orthopedics. It supplies a virtual operation environment through digital medical images for surgeons, provides visual support to make surgical operations more accurate, less invasive, and safer. This technology can track the surgical site and surgical instruments in real time, just like navigating airplanes or ships, so it is called a navigation system.

The current surgical navigation system generally adopts the following principle: a surgeon holds an improved surgical instrument with a traceable mark to perform an operation on the surgical target site. The special positioning and aiming operation of the surgical instrument are monitored by a tracer connected to a computer. At the same time, the tracer must accurately provide the relative relationship between the patient's surgical target site and the preoperative or intraoperative multi-mode images through registration, so as to guide the doctor to operate the surgical instrument and implement the corresponding surgical operation.

The surgical process generally follows the process: obtain patient's preoperative images, such as CT/X-rays images; import them into a computer system to perform necessary processing, such as noise reduction and 3D reconstruction; make a preoperative planning, where doctors make surgical planning based on the patient's conditions, such as nail placement, nail placement angle and depth; perform intraoperative registration, where spatial matching (registration) is based on intraoperative images, a positioning tracer, and preoperative images, to obtain a spatial position relationship between the surgical instrument and the patient's surgical site; establish a simulation model in the monitoring computer to display the position of surgical instrument in real time; perform the operation, track the surgical instruments and the surgical site, and guide the operation according to the preoperative planning.

The navigation systems for orthopedic surgery mostly uses electromagnetic positioning, ultrasonic positioning or optical positioning, and some use gyroscope positioning. For example, a surgical navigation system disclosed in Chinese Patent Application No. 201810430822.1 includes an angle and orientation positioning device installed on surgical instrument, two or more laser projection boards, two or more collectors of laser projection points, and a computer; in the device, the angle and orientation positioning device can detect the current angle of the surgical instrument, and the collectors of laser projection points can collect the position change of the laser beams on the laser projection boards, and then determine the displacement of the surgical instrument in the vertical direction, and obtain the depth of penetration of surgical instrument. However, this technical solution requires a substantial transformation of surgical instrument, and the positioning device is also very complicated. The angle and orientation positioning device installed on the surgical instrument includes a gyroscope, two or more lasers and other components. Both the device itself and the working principle are quite complicated, and registration is difficult.

The registration is the key technology of the navigation system, which can combine the patient's preoperative medical images, the patient's anatomical position information obtained through the intraoperative positioning tracer, and the position information of surgical instrument in the same spatial coordinate system. where the navigation tracer fixed on the patient is used, such as Chinese Patent Application No. 201710970763.2, "A tracer and its connection structure for orthopedic surgery", which includes the groove body for fixing the tracer, a connecting piece and a fixing piece which is fixed on the patient's bony structure. The tracer is pre-designed, is fixed near the bone of the surgical site, and needs an additional space, which results an enlarged open area of the surgery, and increases the patient's pain and is difficult in the operation. Further, the predesigned tracer cannot work well with different bones, it is difficult to fix, which may cause a decrease in navigation accuracy and secondary injury during the operation. With this technology, fluoroscopy image registration is required during the operation, which increases the operation time, and the medical staff and patients are also exposed to more radiation during the operation. The fluoroscopy process requires a C-arm X-ray machine, which takes up a large space and is not applicable for small hospitals.

The navigation tracer of the current orthopedic surgical navigation system has the disadvantages of inconvenient fixation, instability, and difficulty for minimally invasive surgery, or a problem of the complicated positioning of surgical instruments. During the operation, the fluoroscopy registration is generally required, which occupies a greater space, the registration process also prolongs the operation time, and medical staff and patients are exposed to additional radiation.

Therefore, it is necessary to provide a surgical navigation system, a corresponding computer device, and a storage medium that have the advantages of simple and stable registration, high accuracy, simple and easy operation, minimally invasive surgery, flexible space required for surgery site, and low radiation dose.

Technical Problem

An object of the present invention is to provide a surgical navigation system with simple and stable registration, high accuracy, and simple operation, as well as a computer device and a storage medium for performing surgical navigation.

Technical Solution

In order to achieve the object of the present invention, the following technical solutions are provided:

A surgical navigation system is provided, which comprises a positioning marker installing on a surgical instrument, a tracer for fixing on a bone to be operated on, a binocular camera for spatial positioning based on binocular vision, and a graphics workstation computer as a navigation terminal; the tracer comprises at least one navigation tracking surface for navigation and positioning; the positioning marker comprises at least one navigation surface for tracking surgical the instrument; the binocular camera is connected to the computer, and is capable of transmitting the acquired information of the tracer and the positioning marker to the computer.

In accordance with some embodiments, the tracer has at least one bone fitting surface for fitting and fixing to the bone to be operated on. The bone fitting surface is in perfect fit with the bone to be operated on, and the error is small. After the tracer is fixed to the bone, the relative spatial position is unique, and the tracer acts as an extension of the bone. The spatial position of the navigation tracking surface on the tracer is known, therefore, there is no need for fluoroscopic image and registration during the operation, and tracer can be directly used for positioning and tracking.

In accordance with some embodiments, the tracer comprises a surgical guide produced by 3D printing, and the navigation tracking surface is set on the surgical guide. The tracer manufactured by 3D printing can easily and quickly obtain a perfect fit with the bone to be operated on.

The surgical guide comprises a guide body, in accordance with some embodiments, the navigation tracking surface is directly formed on the guide body; or, the navigation tracking surface is arranged on a navigation tracking carrier, and the navigation tracking carrier is arranged on the guide body. The navigation tracking surface is a plane attached with a tracking pattern of visual recognition by visible light, or a plane attached with an imaging sheet with one or more feature points, or a tracking surface formed by a plurality of feature points.

In accordance with some embodiments, the positioning marker is a polyhedron and comprises at least two navigation surfaces. The navigation surfaces can be completely photographed by the binocular camera during the operation, and spatial positioning can be performed by a computer.

In accordance with some embodiments, the computer includes the following units:
- a data receiving and storing unit, used for receiving and storing the information transmitted by the binocular camera; and
- an image reconstruction unit, used for importing and reconstructing a three-dimensional model of the bone to be operated on and a three-dimensional model of the surgical instrument, and using the information acquired by the binocular camera to reconstruct three-dimensional images and postures of the surgical instrument during the operation to obtain visual navigation.

The present invention also provides a computer device, comprising: a memory and a processor; a computer program is stored on the memory; when the computer program is executed by the processor, causes the processor to perform a surgical navigation method, which comprises steps of:
- receiving images of the bone to be operated on and images of a surgical instrument and generating three-dimensional models thereof; obtaining registration information of a tracer fixed on the bone and calibration information of a positioning marker component on the surgical instrument;
- receiving real-time information of the tracer and the positioning marker acquired by a binocular camera;
- calculating spatial position information of the bone to be operated on and the surgical instrument by the binocular vision positioning algorithm according to the real-time information of the tracer and the positioning marker; and fusing the spatial position information with the three-dimensional models in real time; and
- obtaining dynamic images of a real-time positional relationship between the bone and the surgical instrument, so as to obtain surgical navigation.

In accordance with some embodiments, the tracer is provided with at least one navigation tracking surface capable of cooperating with the binocular camera for optical positioning, and the positioning marker includes at least one navigation surface capable of cooperating with the binocular camera for optical positioning.

In accordance with some embodiments, the method comprises: before surgery, designing a three-dimensional model of the tracer and printing the three-dimensional model of the tracer according to the 3D model of the bone to be operated on, and importing an image of the three-dimensional model of the tracer into the computer device.

In accordance with some embodiments, the tracer comprises a surgical guide produced by 3D printing, on which is provided the navigation tracking surface, and the tracer is provided with at least one bone fitting surface for fitting and fixing the bone to be operated.

In accordance with some embodiments, before surgery, performing three-dimensional scanning of the surgical instrument to obtain three-dimensional images thereof, calibrating the positioning marker, and importing the three-dimensional images into the computer device.

In accordance with some embodiments, the positioning marker is a polyhedron and comprises at least two navigation surfaces.

In accordance with some embodiments, the computer is provided with a monitor for real-time display of the calculated dynamic images of the positional relationship between the bone and the surgical instrument.

The present invention also provides a computer-readable storage medium having a computer program stored thereon, and when the computer program is executed by a processor, causes the processor to perform the above-mentioned surgical navigation method.

Advantages

Compared with prior arts, the present invention has the following advantages:
- the technical solution of the present invention is based on the digital navigation technology of visual positioning, the binocular camera cooperates with the tracer on the bone and the positioning marker on the surgical instrument to acquire real-time information of the tracer and the positioning marker; the spatial position information of the bone to be operated on and the surgical instrument is calculated using the binocular vision positioning algorithm, and is fused with the three-dimensional models in real time to obtain the dynamic images of the real-time position relationship between the bone and the surgical instrument to realize the surgical navigation, which can simplify the operation process, improve the accuracy of the operation, reduce the risk of the operation, and realize the personalized treatment needs.

Further, the tracer adopts 3D printing technology to produce a surgical guide that fits the bone surface, because the 3D-printed surgical guide is customized according to the patient's bone, and a fitting surface thereof can perfectly fit the patient's bone with minimal error and being combined with a complex bone stably; the navigation tracking surface and the bone are fixed in a unique relative spatial position, and without registration or intraoperative image support, can be directly used for tracking the operation, which can reduce intraoperative imaging process and simplify the operation process, solve the problem of navigating and positioning patient's anatomy and surgical instrument during orthopedic surgery, optimize the operation process and reduce the use of intraoperative images. The visual navigation can shorten the operation time, reduce radiation to the medical staff and patients during the operation, and reduce the risk of surgery. The surgical navigation system of the present invention is applicable for small and medium-sized hospitals; in addition, the surgical guide generally fits well with the area to be operated on, which enables minimally invasive surgery without additional position fixation.

DETAILED DESCRIPTION OF THE INVENTION

Figure 1:
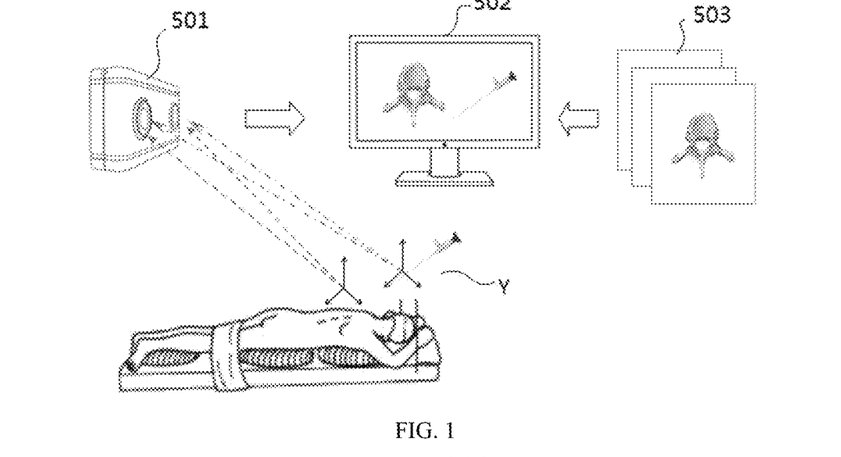
FIG. 1 is a schematic diagram of a surgical navigation system in accordance with a first embodiment of the present invention.
Figure 11:
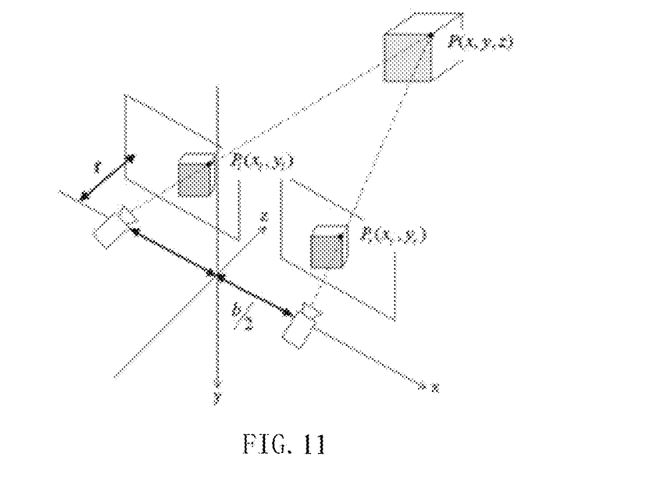
FIG. 11 illustrates the principle of obtaining image information of a tested object by binocular stereo vision.

Please refer to FIG. 1, a surgical navigation system in accordance with an embodiment of the present invention includes a positioning marker (not marked) installing on a surgical instrument, a tracer (not shown) for fixing on the bone to be operated on, and a binocular camera 501 used for spatial positioning based on binocular vision, and a graphics workstation computer 502 used as a navigation terminal. The preoperative images 503 of the bone are imputed into the computer 502. The binocular camera is connected to the computer to transmit the acquired information of the tracer and the positioning marker to the computer, and tracks the tracer and the surgical instrument for spatial positioning based on the visual principle. In the figure, Y represents the reference coordinate of the surgical site of the subject and the surgical instrument. The principle of binocular stereo vision for obtaining the image information of a tested object is shown in FIG. 11.

The main functions of the graphics workstation computer 502 comprise: reconstructing images, importing and reconstructing the 3D model of the patient's bone and the 3D model of the surgical instrument, and storing three-dimensional images (and positioning information) of various surgical instruments, which can be conveniently switched in the operation, such as storing the patient's preoperative CT 3D reconstruction images and the registration information of the 3D-printed tracer; performing real-time image tracking and image fusion, where the images include preoperative CT three-dimensional images and intraoperative three-dimensional images of surgical instruments; receiving real-time images of the binocular camera; and acquiring real-time positioning information of the tracer on the patient and the positioning marker on the surgical instrument by the binocular camera 501 for binocular visual positioning; calculating position and posture information of the 3D-printed tracer and the positioning marking of the surgical instrument by the binocular visual positioning algorithm, and fusing the position information with the three-dimensional images in real time to reconstruct the three-dimensional images and postures of the surgical instruments in the computer, so as to obtain visual navigation during the operation. The graphics workstation computer has functions of identifying boundary or quantifying the deviation in the key operation and provide safe operation.

The computer comprises the following units:
  a data receiving and storing unit, used for receiving and storing the information transmitted by the binocular camera; and
  an image reconstruction unit, used for importing and reconstructing a three-dimensional model of the bone to be operated on and a three-dimensional model of the surgical instrument, and using the information acquired by the binocular camera to reconstruct three-dimensional images and postures of the surgical instrument during the operation to obtain visual navigation.

Please refer to FIGS. 2-9 together, which respectively illustrate the embodiments of the tracer and the positioning marker. The tracer comprises at least one navigation tracking surface used for navigation and positioning, and the positioning marker comprises at least one navigation surface used for tracking surgical the instrument.

Please refer to FIGS. 2-7, the tracer is made by 3D printing. The tracer in the first embodiment includes a guide body 100. A left bone fitting surface 101' and a right bone fitting surface 101 are provided under the guide body. The surgical guide is made based on 3D reconstruction of preoperative bone images. Each bone fitting surface 101 completely fits with a bone surface 302 of the vertebra 300 to be operated on. A navigation tracking surface 200 is also provided on the surgical guide (the tracer), and the navigation tracking surface 200 is directly set on the surface of the guide body 100.

In this embodiment, the tracer defines needle guide holes 103', 103, and fixing holes 104', 104. The fixed holes 104, 104' are used for engaging with screws or other fixing nails to strengthen fixation of the tracer on the vertebra 300 and make the fixation more stable. The needle guide holes 103', 103 are used to guide surgical needles or other instruments. Specifically, the guide body 100 in this embodiment includes a main body 110, a left horizontal base 120' and a right horizontal base 120. The main body 110 is in a shape of an arch, defines a space 102 under the arch for accommodating a spinous process 301 of the vertebrae 300, and comprises: a left arm 1021, a right arm 1022, a top horizontal plane 1023 connecting between the left arm 1021 and the right arm 1022, and a tracking pattern 201 of visual recognition by visible light based on a principle of binocular stereo vision. The tracking pattern 201 is directly formed on the top horizontal plane 1023 and is used for tracking the surgical guide. There is no fixing hole for inserting a screw or a fixing nail defined in any one of the left arm 1021, the right arm 1022 and the top horizontal plane 1023. When the surgical guide is placed on the vertebrae 300, the spinous process 301 is accommodated in the space 102 under the arch, and the arch is not fitted to the spinous process 301 while a gap is left between the arch and the spinous process 301. The left horizontal base 120' horizontally extends from a bottom side of the left arm 1021, forms the left bone fitting surface 101' at a bottom surface of the left horizontal base 120' corresponding to a bone surface at a left side of the spinous process 301 of the vertebra 300, and defines the left fixing hole 104' therethrough for engaging with a screw or a fixing nail to fix a left side of the surgical guide on a left side of the spinous process 301 of the vertebra 300. The right horizontal base 120 horizontally extends from a bottom side of the right arm 1022, forms the right bone fitting surface 101 at a bottom surface of the right horizontal base 120 corresponding to a bone surface at a right side of the spinous process 301 of the vertebra 300, and defines a right fixing hole 104 therethrough for engaging with a screw or a fixing nail to fix a right side of the surgical guide on a right side of the spinous process 301 of the vertebra 300. A left needle guide tube 130' extends upwards from a top surface of the left horizontal base 120', and defines the needle guide hole 103 which extends along a length in the left needle guide tube 130' from a top end of the left needle guide tube 130 to the left bone fitting surface 101' and is used for guiding surgical instruments. The right needle guide tube 130 extends upwards from a top surface of the right horizontal base 120, and defines a needle guide hole 103 which extends along a length in the right needle guide tube 130 from a top end of the right needle guide tube 130 to the right bone fitting surface 101 and is used for guiding surgical instruments. A left horizontal reinforcing beam 105', without a fixing hole therethrough, connects the left needle guide tube 130' and the left arm 1021 of the arch, and is located above the left horizontal base 120'. A right horizontal reinforcing beam 105, without a fixing hole therethrough, connects the right needle guide tube 130 and the right arm 1022 of the arch, and located above the right horizontal base 120. The fixing hole 104 is defined in the base 120. The bone fitting surface 101 is formed at a bottom surface of the base 120, or, the bone fitting surface 101 is provided on any surface of the guide body 100 corresponding to the surface of the bone to be operated on. The base 120 is provided with a needle guide tube 130 and the reinforcing beam 105 connecting the needle guide tube 130 and the main body 110, and the needle guide hole 103 is defined in the needle guide tube 130. The main body 110 is provided with an arch 102 adapted to the spinous process 301 on the vertebrae. An expansion slot 1040 with a side opening 1041 is formed and extends inwards from the top surfaces of the left horizontal base 120' to connect a top end of the left fixing hole 104' for facilitating insertion and accommodation of the screw or the fixing nail into the left fixing hole 104'; and a depth of the left fixing hole is adapted to a length of the screw or the fixing nail. Similarly, an expansion slot 1040 with a side opening 1041 is formed and extends inwards from the top surfaces of the right horizontal base 120 to connect a top end of the right fixing hole 104 for facilitating insertion and accommodation of the screw or the fixing nail into the right fixing hole 104; and a depth of the right fixing hole 104 is adapted to a length of the screw or the fixing nail.

Figure 2:
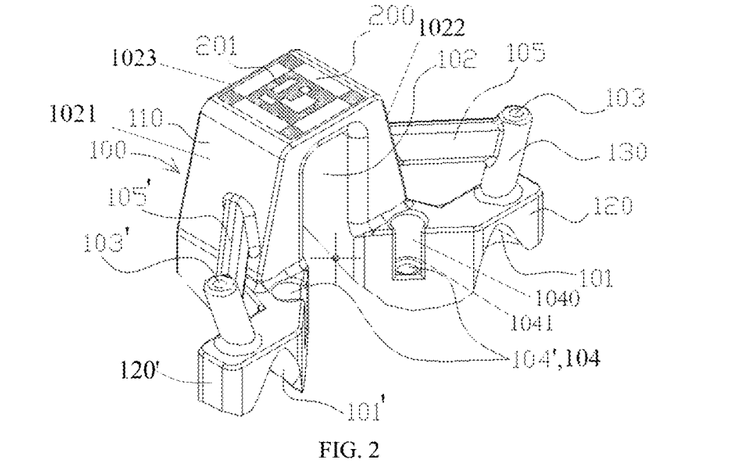
FIG. 2 is a first perspective view of a tracer in the surgical navigation system in accordance with a first embodiment of the present invention.
Figure 3:
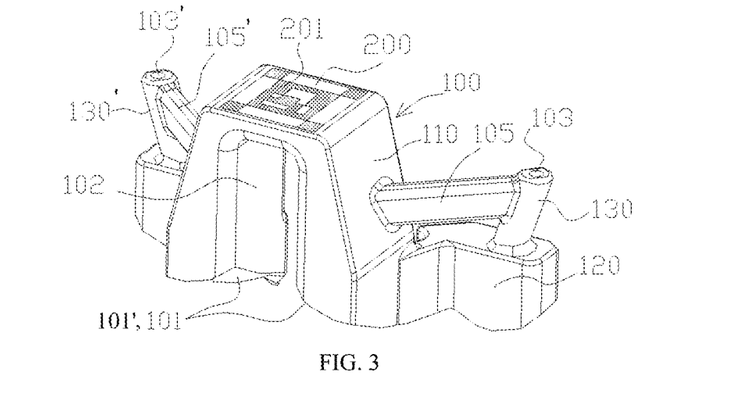
FIG. 3 is a second perspective view of the tracer in the surgical navigation system in accordance with the first embodiment of the present invention.
Figure 4:
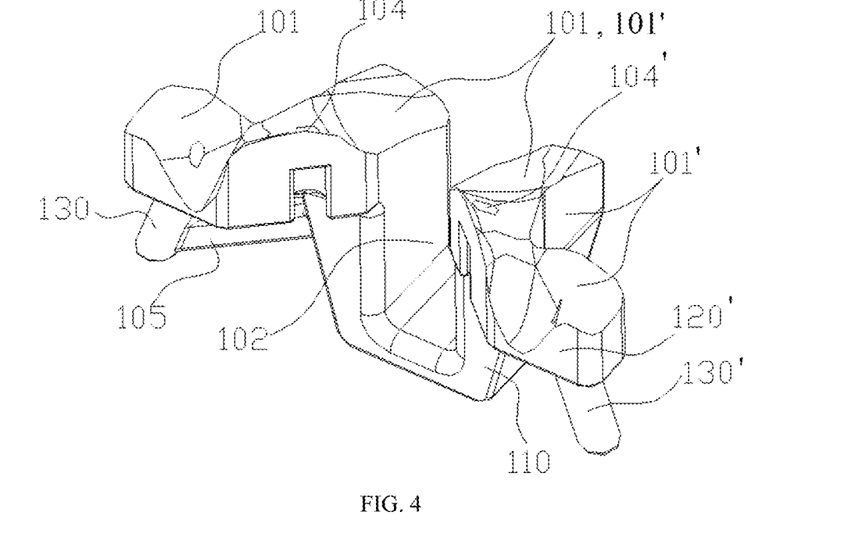
FIG. 4 is a reverse perspective view of the tracer in the surgical navigation system in accordance with the first embodiment of the present invention.
Figure 5:
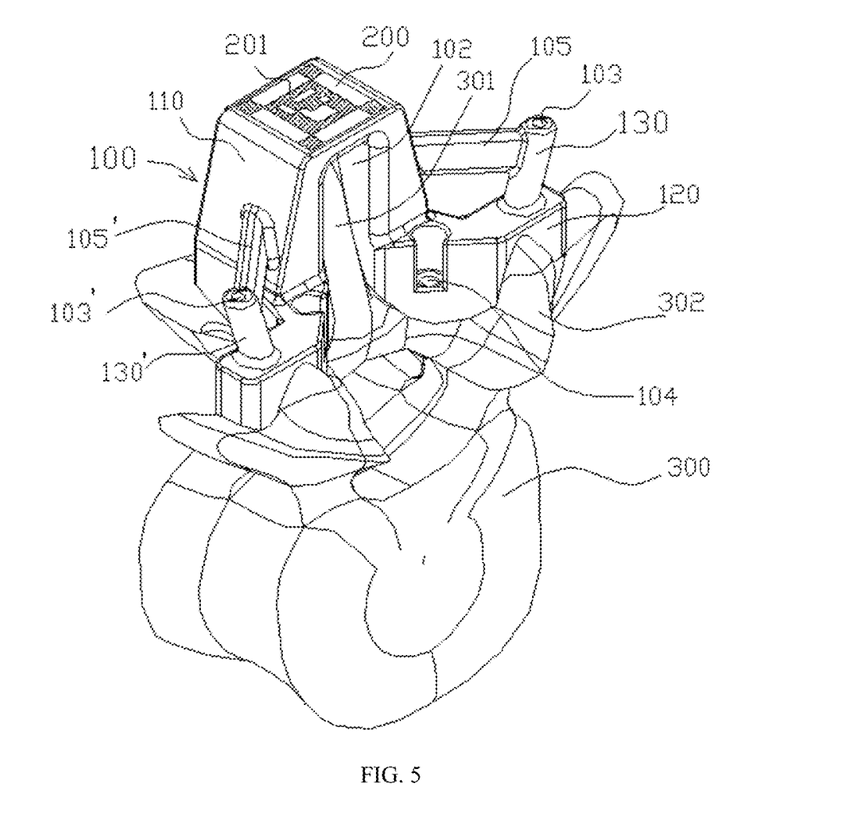
FIG. 5 is a first application diagram of the tracer in the surgical navigation system in accordance with the first embodiment of the present invention.
Figure 6:
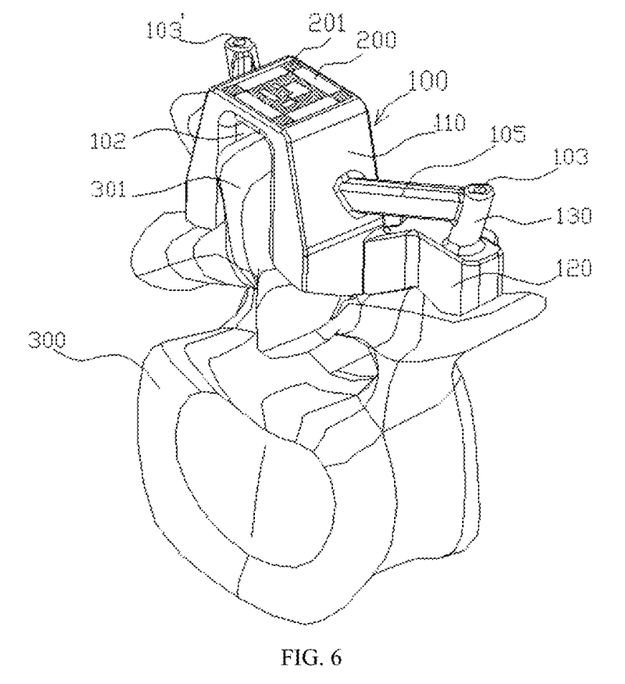
FIG. 6 is a second application diagram of the tracer in the surgical navigation system in accordance with the first embodiment of the present invention.

In this embodiment, the navigation tracking surface 200 is a plane set on the top of the guide body 100, the navigation tracking surface 200 is attached with a tracking pattern 201 of visual recognition by visible light, and the plane is directly formed on the guide body 100.

The tracer is formed by 3D reconstruction of the bone based on the patient's preoperative CT images, and then designing a reverse template consistent with the anatomical shape of the bone using 3D editing software; besides the bone fitting surface and auxiliary structures, the navigation tracking surface 200 is set on the top of the surgical guide, and a tracking pattern 201 of visual recognition by visible light is set on the navigation tracking surface 200. In other embodiments, feature points, reflective points, etc. can also be set for intraoperative registration or navigation.

The technical solutions of the present invention can make the guide body with the navigation tracking surface thereon stably fixed to the complex bone, adapt to different parts of the bone of different patients without deviation, provide high navigation accuracy, reduce the intraoperative imaging, and simplify the surgical process. The registration and tracking of the spatial position within the surgical area can be obtained through the pattern or feature marking points on the navigation surface. The navigation tracking surface is designed according to the navigation requirements. For example, the navigation tracking surface is a plane with a minimum of 10*10 mm and is attached with a tracking pattern of visual recognition by visible light. There are also many other technical methods for registration and tracking, such as X-ray, infrared and so on. In other embodiments, there may be no fixing holes or needle guide holes defined in the trace. The needle guide hole is used to guide surgical instruments during surgical drilling or nail placement. When digital navigation or surgical robots are used, the position and angle of the drilling or nail placement have been determined through preoperative or intraoperative planning, therefore, the needle guide hole may be not set.

Figure 7:
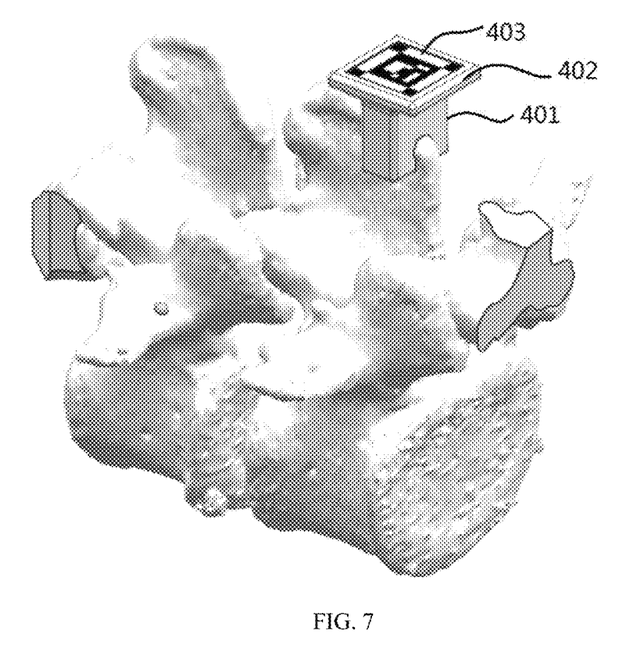
FIG. 7 is a first application diagram of the tracer in the surgical navigation system in accordance with a second embodiment of the present invention.

As shown in FIG. 7, in the second embodiment, the tracer includes a guide body 401 and a navigation tracking surface thereon. The guide body 401 is directly fixed on the bone, is attached to the bone with a complete fit between the bone fitting surface of the guide body and the bone surface, so that the tracer can be clamped at the spinous process of the vertebra. The guide body 401 is provided with a platform 402 as a navigation tracking carrier, and the platform 402 is provided with a tracking pattern 403 of visual recognition by visible light.

The bone fitting surface is in perfect fit with the bone to be operated on, and the error is small. After the tracer is fixed to the bone, the relative spatial position is unique, and the tracer acts as an extension of the bone. The spatial position of the navigation tracking surface on the tracer is known, therefore, there is no need for fluoroscopic image and registration during the operation, and tracer can be directly used for positioning and tracking.

Figure 8:
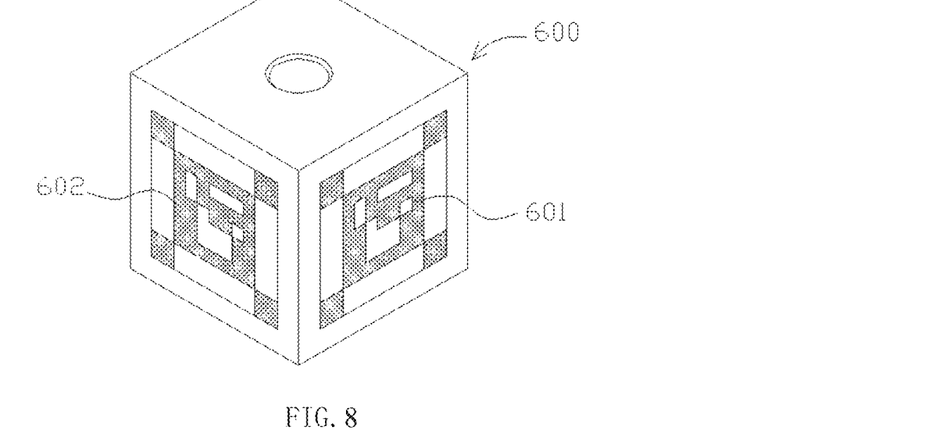
FIG. 8 is a schematic diagram of a positioning marker in the surgical navigation system in accordance with a first embodiment of the present invention.
Figure 9:
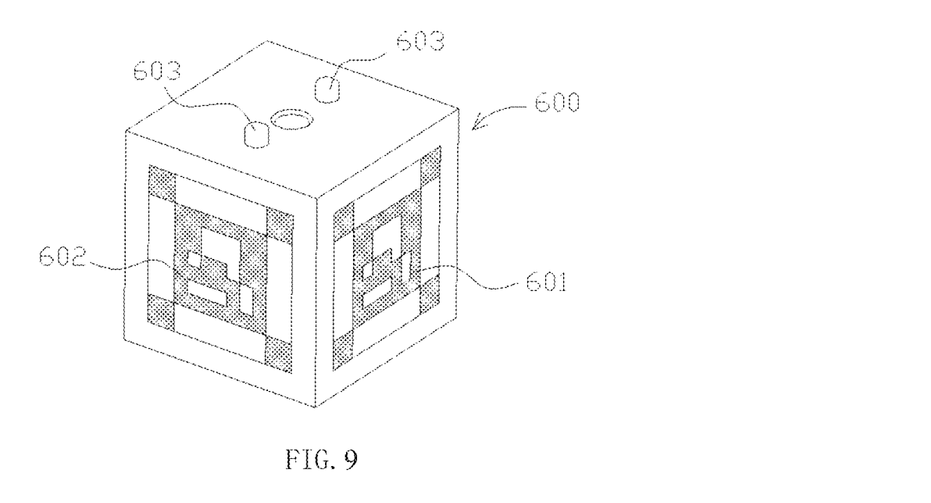
FIG. 9 is a schematic diagram of the positioning marker in the surgical navigation system in accordance with a second embodiment of the present invention.

Referring to FIGS. 8 and 9, a positioning marker 600 installed on a specific part of the surgical instrument, is a polyhedron and has at least two navigation surfaces 601 and 602. The navigation surfaces can be completely photographed by the binocular camera during the operation, and spatial positioning can be performed by a computer. Compared with the first embodiment in FIG. 8, positioning posts 603 are set for fixed and positioning in the second embodiment in FIG. 9.

The positioning marker 600 can also be manufactured using 3D printing. Design a 3D structure of the positioning marker that matches the 3D model of the surgical instrument using 3D editing software, and then manufacture the positioning marker by 3D printing and fix it to the surgical instrument. The positioning marker may also have more than two navigation surfaces thereon, for example, there are 3 or 4 navigation surfaces. The number of navigation surfaces depends on the operating requirements of the surgical instrument. Visual tracking and positioning require a complete shot of one navigation surface.

Figure 10:
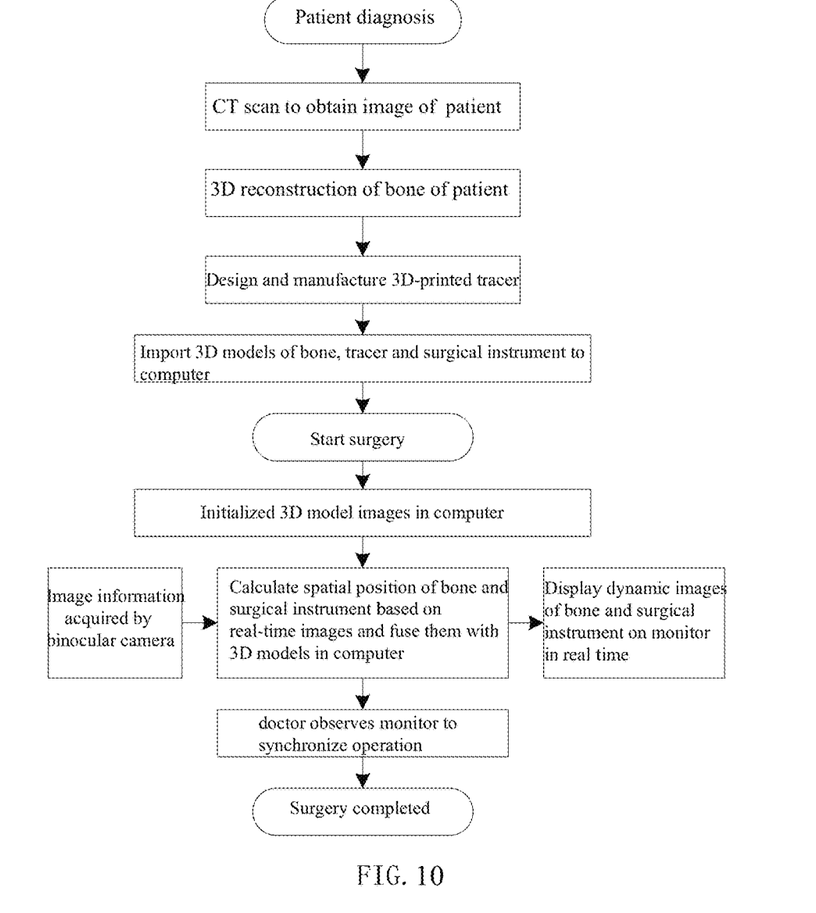
FIG. 10 is a flowchart of a surgical navigation method executed by a computer program in the present invention.

Please refer to FIGS. 1 to 10 together, the method of applying the surgical navigation system of the present invention for surgical navigation, mainly comprises steps of:

receiving images of the bone to be operated on and images of a surgical instrument and generating three-dimensional models thereof; obtaining registration information of a tracer fixed on the bone and calibration information of a positioning marker on the surgical instrument;

receiving real-time information of the tracer and the positioning marker acquired by a binocular camera;

calculating spatial position information of the bone to be operated on and the surgical instrument by the binocular vision positioning algorithm according to the real-time information of the tracer and the positioning marker; and fusing the spatial position information with the three-dimensional models in real time; and obtaining dynamic images of a real-time positional relationship between the bone and the surgical instrument, so as to obtain surgical navigation.

The tracer and the positioning marker on the surgical instrument are disclosed as the above-mentioned embodiments, and the optical positioning method are performed between the binocular camera and both the positioning marker of the tracer and the surgical instrument. Use dual cameras or multiple cameras to observe the target, and then reconstruct the spatial position of the target based on the principle of vision. The device occupies a small space and has high accuracy. Binocular stereo vision is based on the principle of parallax, and is a method as illustrated in FIG. 11, comprising: acquiring two images of the tested object from different positions by imaging device, and obtaining the three-dimensional geometric information of the tested object by calculating the position deviation between the corresponding points of the images.

Specifically, as shown in FIG. 1 and FIG. 10, taking a navigation method for a spine surgery as an example, the method comprises steps of: first: performing a diagnosis for the subject, obtaining bone images through CT scan before surgery, and performing 3D reconstruction of the bone in a computer device; obtaining a 3D-printed tracer by: performing 3D reconstruction of the bone and editing the model thereof based on the bone images acquired before surgery, and then printing by a 3D printer; wherein during the operation, the doctor makes an incision at the patient's surgical site and peels off the soft tissue, and fixes the tracer on the bone of the patient, then the tracer becomes an extension of the bone, and the tracking pattern on the navigation tracking surface can be optically positioned; performing three-dimensional scanning of surgical instruments to obtain three-dimensional images thereof, installing the positioning marker, calibrating the positioning marker, where the positioning marker installed to the surgical instrument has 2 to 4 navigation surfaces which can be optically positioned with the 3D-printed tracer; and importing the 3D models of the bone, the tracer and the surgical instrument into the computer.

During the operation, the navigation method comprises: initializing the images of the 3D models in the computer, acquiring images through the binocular camera, tracking the spatial position information of the tracer and the surgical instrument, transmitting the acquired video data to the computer in real time by the binocular camera connected to the computer, calculating the relative positional relationship between the bone of the subject and the surgical instrument according to the real-time images by the binocular vision positioning algorithm in the computer, fusing the position information of the surgical instrument and the bone with the 3D models of the bone and the surgical instrument obtained from the preoperative images, obtaining real-time dynamic images of the positional relationship between the bone and the surgical instrument, and displaying the dynamic images of the bone and the surgical instrument in real time through a monitor connected to the computer, so that doctors can perform the surgery by observing the monitor, thereby a visual navigation for the surgery is obtained.

Before surgery, the navigation method comprises: performing CT scan and 3D reconstruction of the surgical site of the subject, and then designing and producing the 3D-printed tracer (surgical guide) using 3D editing software, wherein the models of the bone and the tracer are imported to the graphics workstation computer of the surgical system before surgery; and before surgery, the surgical instrument to be used in the operation has been scanned in three dimensions and imported into the computer (or the library of the surgical instruments to be prepared); calibrating the navigation markers to make the posture and position error within an acceptable range.

The computer mainly executes the real-time fusion of images and the quantitative monitoring of the position information of the surgical instrument; specifically comprising steps of: first, accepting initial instructions to start 3D reconstruction of the images of the bone and fuse the 3D images of the surgical instrument; during the operation, receiving the real-time images from the binocular camera and analyze to obtain the position information of the surgical site and the surgical instrument, and fusing the images of the 3D model with the position information and display on the navigation display.

The present invention also provides a computer device, comprising a memory and a processor, and a computer program is stored on the memory. When the computer program is executed by the processor, causes the processor to perform the above-mentioned surgical navigation method.

The present invention also provides a computer-readable storage medium having a computer program stored thereon, and when the computer program is executed by a processor, causes the processor to perform the above-mentioned surgical navigation method.

The surgical navigation system of the present invention can be applied to spinal surgery, pelvic or thoracic spine surgery, joint surgery, trauma surgery, bone tumor or orthopedic surgery.

The foregoing are only preferred embodiments of the present invention, and the scope of protection of the present invention is not limited thereto. Any equivalent transformation based on the technical solution of the present invention shall fall within the protection scope of the present invention.

What is claimed is:

1. A surgical guide, used for an operation on a subject's vertebra, comprising: a main body, which is in a shape of an arch and defines a space under the arch for accommodating a spinous process of the vertebrae; comprising: a left arm; a right arm; a top horizontal plane, connecting between the left arm and the right arm; and a tracking pattern of visual recognition by visible light based on a principle of binocular stereo vision, which is directly formed on the top horizontal plane and is used for being photographed by a binocular camera to obtain dynamic images of real-time position relationship between the vertebrae and a surgical instrument to track the surgical guide and realize a surgical navigation; when the surgical guide is placed on the vertebrae, the spinous process is accommodated in the space under the arch, and the arch is not fitted to the spinous process while a gap is left between the arch and the spinous process; a left horizontal base, horizontally extending from a bottom side of the left arm, forming a left bone fitting surface at a bottom surface of the left horizontal base corresponding to a bone surface at a left side of the spinous process of the vertebra, and defining a left fixing hole therethrough for engaging with a screw or a fixing nail to fix a left side of the surgical guide on the left side of the spinous process of the vertebra; a right horizontal base, horizontally extending from a bottom side of the right arm, forming a right bone fitting surface at a bottom surface of the right horizontal base corresponding to a bone surface at a right side of the spinous process of the vertebra, and defining a right fixing hole therethrough for engaging with a screw or a fixing nail to fix a right side of the surgical guide on the right side of the spinous process of the vertebra; a left needle guide tube, extending upwards from a top surface of the left horizontal base, and defining a needle guide hole which extends along a length in the left needle guide tube from a top end of the left needle guide tube to the left bone fitting surface and is used for guiding surgical instruments; a right needle guide tube, extending upwards from a top surface of the right horizontal base, and defining a needle guide hole which extends along a length in the right needle guide tube from a top end of the right needle guide tube to the right bone fitting surface and is used for guiding surgical instruments; a left horizontal reinforcing beam, without a fixing hole therethrough for inserting a screw or a fixing nail, connecting the left needle guide tube and the left arm of the arch, and located above the left horizontal base; and a right horizontal reinforcing beam, without a fixing hole therethrough for inserting a screw or a fixing nail, connecting the right needle guide tube and the right arm of the arch, and located above the right horizontal base; wherein the surgical guide is made by 3D printing based on 3D reconstruction of preoperative bone images; each of the left bone fitting surface and the right bone fitting surface is used to be completely fitted to and stably combined with the bone surface of the vertebra to be operated on; during the operation, the surgical guide with the tracking pattern is fixed to the vertebra, the tracking pattern is fixed in a unique relative spatial position on the vertebra and directly used for navigating and positioning a surgical site of the subject and surgical instrument during the operation.

2. The surgical guide of claim 1, wherein the surgical guide is produced that: perform the 3D reconstruction of the vertebrae to be operated on based on preoperative CT images of the vertebrae, design a reverse template consistent with an anatomical shape of the vertebrae using 3D editing software as three-dimensional model of the surgical guide, and print the three-dimensional model of the surgical guide by a 3D printer to obtain the surgical guide.

3. The surgical guide of claim 1, wherein the tracking pattern is capable of cooperating with the binocular camera for optical positioning; the binocular camera is connected to a computer; during the operation, the tracking pattern is photographed by the binocular camera to obtain real-time images, the computer calculates a relative spatial positional relationship between the vertebrae of the subject and the surgical instruments according to the real-time images, and fuses the relative spatial positional relationship with three-dimensional models of the vertebrae and the surgical instrument in real time to obtain the dynamic images of real-time position relationship between the vertebrae and the surgical instrument to realize the surgical navigation.

4. The surgical guide of claim 1, wherein an expansion slot with a side opening is formed and extends inwards from the top surface of the left horizontal base to connect a top end of the left fixing hole for facilitating insertion and accommodation of the screw or the fixing nail into the left fixing hole; and a depth of the left fixing hole is adapted to a length of the screw or the fixing nail.

5. The surgical guide of claim 4, wherein an expansion slot with a side opening is formed and extends inwards from the top surface of the right horizontal base to connect a top end of the right fixing hole for facilitating insertion and accommodation of the screw or the fixing nail into the right fixing hole; and a depth of the right fixing hole is adapted to a length of the screw or the fixing nail.

* * * * *